United States Patent
Khoury et al.

(10) Patent No.: US 6,257,890 B1
(45) Date of Patent: *Jul. 10, 2001

(54) GINGIVA FORMER

(75) Inventors: Fouad Khoury, Muenster; Joerg Neugebauer, Heidelberg, both of (DE)

(73) Assignee: Friadent GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,441

(22) Filed: Mar. 18, 1999

(30) Foreign Application Priority Data

Jul. 10, 1998 (EP) .................................. 98112827

(51) Int. Cl.[7] .................................. A61C 8/00
(52) U.S. Cl. .................................. 433/173
(58) Field of Search .................................. 433/172, 173, 433/174; 606/232

(56) References Cited

U.S. PATENT DOCUMENTS

| | | | |
|---|---|---|---|
| 3,664,345 | * | 5/1972 | Dabbs et al. . |
| 4,856,994 | | 8/1989 | Lazzara et al. . |
| 4,872,840 | | 10/1989 | Bori . |
| 4,988,351 | | 1/1991 | Paulos et al. . |
| 5,839,899 | * | 11/1998 | Robinson .................................. 433/173 |
| 5,921,774 | * | 7/1999 | Kanomi et al. .................................. 433/173 |

FOREIGN PATENT DOCUMENTS

| | | |
|---|---|---|
| 3300764 A1 | 7/1984 | (DE) . |
| 891748 A1 | 1/1999 | (EP) . |

* cited by examiner

*Primary Examiner*—Ralph A. Lewis
(74) *Attorney, Agent, or Firm*—Crowell & Moring, L.L.P.

(57) ABSTRACT

The invention relates to a gingiva former which can be connected to a dental implant and has a head portion (2) which is located in the region of the gingiva. The gingiva former should be developed such that the formation of the soft tissue be improved. Thus it is suggested that the head portion (2) have at least one opening (14) for gingival fastening devices and that the opening (14) lead into a central bore (6) of the head portion (2).

23 Claims, 2 Drawing Sheets

GINGIVA FORMER

BACKGROUND OF THE INVENTION

The invention relates to a gingiva former.

A gingiva former of this type which can be connected to a dental implant is known from U.S. Pat. No. 4,856,994. After the implant has had time to heal, a reopening is effected by means of a scalpel, an electrotome or a mucosa cutter to allow a screw cap connected to the dental implant to be removed from the implant and replaced by the gingiva former. The exterior of the gingiva former known from the U.S. patent is cylindrical, although today gingiva formers with differently shaped exteriors are also known. In another healing phase which follows the reopening, the gingiva former enables the efficient formation of the mucous border. It must be ensured that after the insertion of the crown structure, the gums lie against its gingival band in a way that is sealed against bacterial entry. Gingiva formers are provided which are appropriate matches for dental implants with varying diameters, and gingiva formers with appropriate heights are also available depending on the respective height of the gums. Problems can occur, however, if during the healing phase the mucosa doesn't fit in the desired way and the mucous border doesn't form in the desired way with respect to the exterior shape of the gingiva former. Thus, the fitting of the mucosa to the gingiva former can only be partially attained by local lifting of regions of the mucous membrane. Unacceptably large gaps between the gingiva former and mucosa can occur such that the desired tight seal cannot be assured long-term after the healing of the gums and then insertion of the transfer structure and after the completion of the superstructure.

Furthermore, a dental implant with a conical top piece is known from U.S. Pat. No. 4,872,840. A membrane can be placed between the top piece and the of the body of the implant. On the side facing the body of the implant, the diameter of the conical top piece is essentially equal in size to the coronal end of the body of the implant. On the side of the head facing away from the body of the implant, the conical top piece has a substantially smaller diameter. In the region of the side of the head mentioned, slits are provided for the fastening of structures which enable stabilization during the healing phase. After the healing phase, a cap for attaching a crown structure or similar object is arranged on the top piece, where the aforementioned slits of the top piece enable a dental cement or some such thing to be fixed thereon.

Furthermore, a gingiva former is known from DE-A-33 00 764 which has a threaded bore in the side facing away from the dental implant. A key can be placed into this threaded bore either in order to insert the gingiva former into the dental implant or to extract it from the dental implant.

Finally, a bone screw with a washer for attaching tissue is known from U.S. Pat. 4,988,351. This washer has passage holes for receiving sutures, which holes run at an angle to its longitudinal axis. Pointing radially inwards, these passage holes end in a conical region which serves as a rest for the screw head. The washer is laid on its outer surface in order to attach the tissue.

SUMMARY OF THE INVENTION

Therefore, it is the object of the invention to avoid the aforementioned disadvantages and to further develop a gingiva former such that the formation of the soft tissue is improved. The gingiva former should simple and functional to handle. Additionally, it should be easy to produce and enable the gingiva to be attached without difficulty.

This object is achieved by a gingiva former as described and claimed hereinafter.

The gingiva former according to the invention distinguishes itself by its functional construction and simple structure. At least one opening for introducing means for fastening the gingiva is located in its head portion. The opening is preferably designed as a slit or passage hole which leads to a central bore and into which normal dental materials can be introduced, particularly in order to be able to stitch appropriately prepared flaps of mucosa. The end face of the head portion contains the central, axial bore, which is designed as a through bore for a mounting screw or as a blind bore for engagement means of a tool used to screw the gingiva former into the body of the implant, which is embedded in the jaw bone. The slits or openings designed for use with the dental materials mentioned begin radially outwards in the side wall of the gingiva former, which wall preferably is essentially cylindrical and coaxial with respect to the longitudinal axis, and end in the central bore mentioned previously. Additionally, the slits or openings mentioned preferably are arranged essentially at a right angle with respect to the longitudinal axis, however, within the scope of the invention, they can also be inclined at a pre-determinable angle with respect to the longitudinal axis. The gingiva former has, on one hand, a head with a side wall for placement of the gingiva and, on the other, a shaft for anchoring itself in the implant body. In a particular embodiment, the shaft has an outer thread for screwing into a corresponding inner thread of a recess in the implant body. In this case, the engagement means for a tool for screwing in the device are preferably located axially between the shaft and the openings, particularly designed as radial, which are provided for the dental materials mentioned. In another embodiment, the shaft is provided with contact faces, preferably having the contour of a polygon, particularly a hexagon, which keep it from turning with respect to the body of the implant.

Preferably, the at least one slit or opening or through bore is arranged in a radial plane which is substantially perpendicular to the longitudinal axis. In this case, the slit or opening preferably ends at the central bore which is provided coaxial to the longitudinal axis. Additionally, the slits or openings are advantageously arranged in the upper end region of the head portion, particularly in the upper half of the head portion, advantageously in the upper third adjacent to the free end or end face of the head portion.

Embodiments and specific developments of the invention are described in the subclaims as well as in the following specification.

BRIEF DESCRIPTION OF THE DRAWINGS

The invention will be explained hereinafter in further detail with reference to the illustrative embodiments shown in the drawings, without limiting the invention in this respect.

DETAILED DESCRIPTION OF PREFERRED EMBODIMENTS

Figure 1:
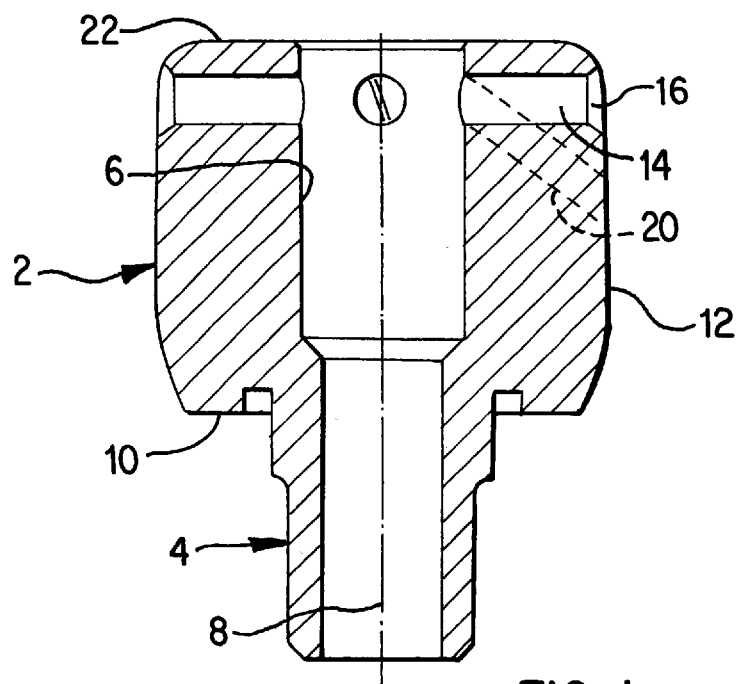
FIG. 1 shows an axial section through of the gingiva former with through bores arranged in a radial plane.

In an axial cross section, FIG. 1 shows the gingiva former with a head portion 2, a shaft 4 and a central bore 6 which is coaxial with respect to the longitudinal axis 8. The central bore 6 is designed as a through bore into which a locking screw, not shown, can be inserted for connection with an implant body, also not shown, which can be anchored in the jaw bone. The head portion 2 is disposed in the region which penetrates through the gingiva. On its lower end 10, the head portion 2 has an outer diameter which essentially corresponds to the outer diameter of the coronal end of the implant body. When the gingiva former is connected to the implant body, the head portion 2 is freely accessible, whereas the shaft is located inside a receiver opening in the implant body. The head portion 2 is designed to be rotationally symmetrical with respect to the longitudinal axis 8, wherein, according to the invention, the upper portion of the side wall 12 is cylindrical, and the lower portion is rounded off in a slight dome.

The head portion 2 contains several, in particular four, openings 14 which are designed as through bores and which enable the attachment of the mucosa with appropriate fastening devices, such as dental suturing materials in particular. The openings 14 lie advantageously in the upper end region and/or in the upper half, preferably in the upper third of the head portion 2. The openings 14 begin radially outwards in the side wall 12, pass through the head portion 2 and end in the central bore 6. The outer radial ends of the through bores 14 lie in the outer side wall 12. There, the radial passage holes are flared outward by means of beveled edges 16 to ease the introduction of the devices for fastening the gingiva.

In an alternative embodiment of the invention, the radial passage holes 14 are not arranged in a radial plane at a right angle to the longitudinal axis 8. As shown by means of the broken lines 20, the through bores are inclined at a predetermined angle to the longitudinal axis 8. In this embodiment, the aforementioned bores 20 also begin radially outwards in the side wall 12, pass through the head 2 and end in the central bore 6.

Figure 2:
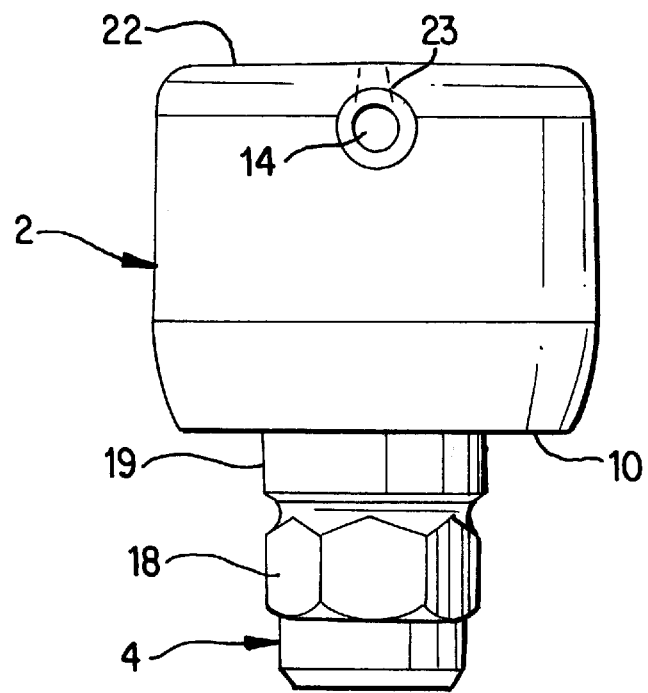
FIG. 2 shows a side view of the illustrative embodiment according to FIG. 1.

As can be seen in FIG. 2, the shaft 4, which is inserted in the implant body, has flattened surfaces 18 on its sides which form a hexagon for the purpose of keeping the gingiva former from turning with respect to the implant body, into whose corresponding receiver opening the shaft 4 of the gingiva former is inserted. Naturally, the shaft 4 can also have other means which prevent its rotation.

Preferably, adjacent to the bottom end 10 of the head 2, the shaft 4 contains a specifically cylindrical centering band 19. In addition, the gingiva former according to the invention can also be designed without a shaft and can have a recess in a side facing the implant body for preventing rotation and aligning the implant body. In this type of embodiment, a corresponding pin on the implant body with means to prevent rotation and align the gingiva former, protrudes into the aforementioned recess. Furthermore, the gingiva former can have teeth in the region of its bottom end 10 or comparable means for preventing rotation.

In an alternate embodiment, the openings 14 are designed as slits which open upwards toward end face 22. As shown with broken lines 23, the side walls of the slit are preferably inclined such that the slit width is smallest at the end face. This prevents the unwanted slipping out of the means for holding the gingiva. The slits which open onto the face 22 allow the fastening means to be inserted without difficulty.

Figure 3:
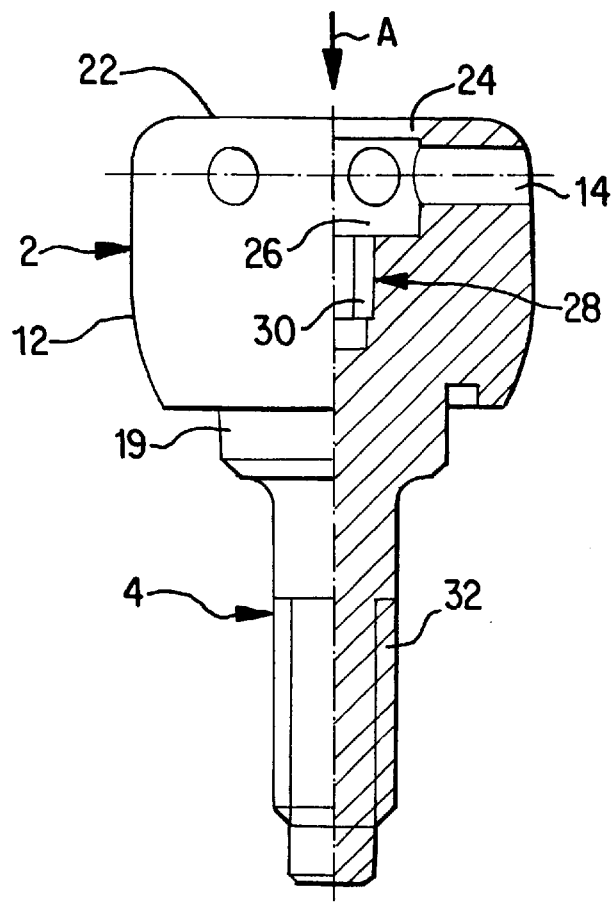
FIG. 3 shows another illustrative embodiment of the gingiva former which can be screwed into an implant body.

FIG. 3 shows a particular exemplary embodiment of the gingiva former whose central bore 6 is designed as a blind bore in the head portion 2. The central bore 6 has a beveled edge 24 in the region of the face 22 which adjoins a first upper region 26 cervically. The through bores 14 for the fastening means for the gingiva open into this upper region 26. The upper region 26 is preferably designed as a cylinder. In addition, the central bore 6 has, especially adjacent to the expanded upper region 26, an engagement region 28 for engagement means, by which the gingiva former can be screwed into the implant body. The engagement region has at least one contact face 30 for a tool for turning. Advantageously, several similar contact faces 30, essentially parallel to the axis, are located around the circumference in the shape of a polygon, in particular a hexagon. Preferably, the engagement region has a smaller diameter, preferably substantially smaller, than the upper region 26. The central bore 6, designed as a blind bore, therefore has a stepped inner contour. Because of the substantially larger diameter of the upper region 26, into which the side openings 14 lead, it is particularly easy to access the means for fastening the gingiva. The shaft 4 has an external thread 32, with which the gingiva former can be screwed into a corresponding internal thread of the implant body. In such case, a device for screwing, for example an Allen wrench, is inserted into the engagement area 28, where the screwing-in motion is executed by turning around the longitudinal axis 8. In order to center the device, a centering band 19 is provided adjacent the bottom end 10 of the head 2.

Figure 4:
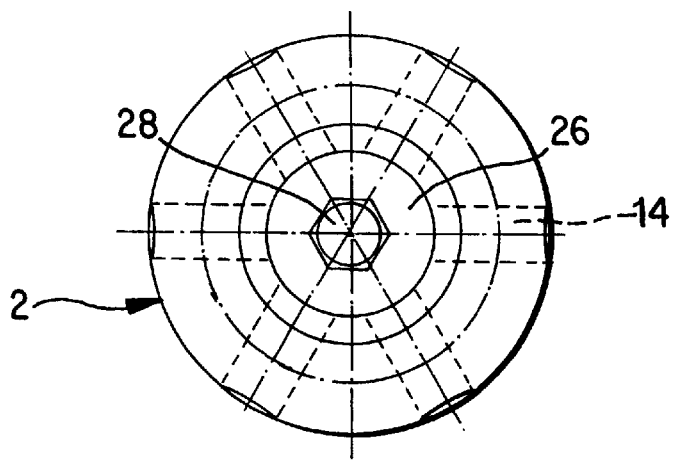
FIG. 4 shows a view of the gingiva former according to FIG. 3 in the viewing direction A.

FIG. 4 shows a top plan view of the gingiva former in which the total of six radial through bores 14 are shown by broken lines. As can be seen, these through bores 14, distributed at regular intervals around the circumference, end in the upper, expanded region 26 of the central blind bore. Furthermore, it is easy to recognize the engagement region 28, in particular designed as a hexagon, which adjoins the upper region 26 cervically.

What is claimed is:

1. A gingiva former for connection to a dental implant, said gingiva former comprising:
   a head portion to be positioned in the region of gingiva of a patient, said head portion having a central bore and being provided with at least on opening for receiving means for fastening the gingiva, each said at least one opening leading into said central bore of said head portion; and
   a shaft portion extending from the head portion for securing the gingiva former to the dental implant;
   wherein the shaft portion extending from the head portion includes a centering band adjacent the head portion.

2. A gingiva former according to claim 1, wherein each said at least one opening is a slit which is open toward a top end surface of the head portion.

3. A gingiva former according to claim 1, wherein each said at least one opening is arranged in an upper portion of said head portion adjacent a top end surface of said head portion.

4. A gingiva former according to claim 1, wherein said at least one opening comprises a plurality of openings distributed substantially uniformly around an axis of said central bore of said head portion.

5. A gingiva former according to claim 4, wherein said head portion is provided with four openings distributed uniformly around the axis of the central bore of the head portion.

6. A gingiva former according to claim 1, wherein said head portion has a cylindrical side wall, and each said at least one opening extends from said cylindrical side wall to said central bore.

7. A gingiva former according to claim 1, wherein each said at least one opening is arranged inclined at a predetermined angle with respect to an axis of said central bore of the head portion.

8. A gingiva former according to claim 7, wherein each said at least one opening is arranged inclined at an angle between 30° and 60° with respect to the axis of said central bore of the head portion.

9. A gingiva former according to claim 8, wherein each said at least one opening is arranged inclined at an angle between 40° and 50° with respect to the axis of said central bore of the head portion.

10. A gingiva former according to claim 9, wherein each said at least one opening is arranged inclined at an angle of about 45° with respect to the axis of said central bore of the head portion.

11. (Amended) A gingiva former according to claim 1, wherein said central bore has an upper region into which each said at least one opening opens, and said central bore is provided with a conical beveled edge opening toward a top end surface of the head portion.

12. A gingiva former according to claim 11, wherein said shaft portion is an externally threaded shaft portion which can be screwed into an internally threaded aperture in the implant, and wherein said gingiva former further includes an engagement area adjacent an upper region of the head portion for receiving a turning tool for screwing the shaft portion of the gingiva former into the implant.

13. A gingiva former according to claim 12, wherein the diameter of said upper region is greater than the diameter of the engagement area.

14. A gingiva former according to claim 12, wherein said engagement region has a polygonal configuration.

15. A gingiva former according to claim 14, wherein said engagement region has a hexagonal configuration.

16. A gingiva former according to claim 1, wherein said central bore in a blind bore.

17. A gingiva former for connection to a dental implant, said gingiva former comprising:
    a head portion to be positioned in the region of gingiva of a patient, said head portion having a central bore and being provided with at least on opening for receiving means for fastening the gingiva, each said at least one opening leading into said central bore of said head portion; and
    a shaft portion extending from the head portion for securing the gingiva former to the dental implant;
    wherein each said at least one opening is a through bore extending from a side surface of said head portion into said central bore.

18. A gingiva former for connection to a dental implant, said gingiva former comprising:
    a head portion to be positioned in the region of gingiva of a patient, said head portion having a central bore and being provided with at least on opening for receiving means for fastening the gingiva, each said at least one opening leading into said central bore of said head portion; and
    a shaft portion extending from the head portion for securing the gingiva former to the dental implant;
    wherein each said at least one opening is a through bore arranged in a radial plane perpendicular to the axis of said central bore of the head portion.

19. A gingiva former for connection to a dental implant, said gingiva former comprising:
    a head portion to be positioned in the region of gingiva of a patient, said head portion having a central bore and being provided with at least one opening for receiving means for fastening the gingiva, each said at least one opening leading into said central bore of said head portion; and
    means for preventing rotation of said head portion with respect to said implant, wherein said means for preventing rotation is positioned on an end surface of said head portion facing said implant and includes an axial through-bore for screwing attachment to said implant.

20. The gingiva former according to claim 19, wherein the means for preventing rotation includes a plurality of flat sections.

21. A gingiva former for connection to a dental implant, said gingiva former comprising:
    a head portion to be positioned in the region of gingiva of a patient, said head portion having a central bore and being provided with at least one opening for receiving means for fastening the gingiva, each said at least one opening leading into said central bore of said head portion; and
    a securing portion extending from the head portion for securing the gingiva former to the dental implant;
    wherein the securing portion extending from the head portion includes a centering band adjacent the head portion.

22. A gingiva former for connection to a dental implant, said gingiva former comprising:
    a head portion to be positioned in the region of gingiva of a patient, said head portion having a central bore and being provided with at least one opening for receiving means for fastening the gingiva, each said at least one opening leading into said central bore of said head portion; and
    a securing portion extending from the head portion for securing the gingiva former to the dental implant;
    wherein said securing portion comprises means for preventing rotation of said head portion with respect to said implant, wherein said means for preventing rotation is positioned on an end surface of said head portion facing said implant and includes an axial through bore for screwing attachment to said implant.

23. The gingiva former according to claim 22, wherein the means for preventing rotation includes a plurality of flat sections.

* * * * *